(12) United States Patent
Watanabe et al.

(10) Patent No.: US 8,445,123 B2
(45) Date of Patent: May 21, 2013

(54) LUBRICANT FOR MAGNETIC RECORDING MEDIA, AND MAGNETIC RECORDING MEDIUM USING THE LUBRICANT

(75) Inventors: Takeshi Watanabe, Nagano (JP); Kunihiro Imai, Nagano (JP); Akira Furuta, Nagano (JP); Kazuo Nimura, Nagano (JP); Hideki Kina, Nagano (JP)

(73) Assignee: Fuji Electric Co., Ltd. (JP)

( * ) Notice: Subject to any disclaimer, the term of this patent is extended or adjusted under 35 U.S.C. 154(b) by 976 days.

(21) Appl. No.: 12/407,035

(22) Filed: Mar. 19, 2009

(65) Prior Publication Data

US 2009/0239099 A1  Sep. 24, 2009

(30) Foreign Application Priority Data

Mar. 19, 2008 (JP) .................. 2008-070534

(51) Int. Cl.
*G11B 5/66* (2006.01)
(52) U.S. Cl.
USPC ....................... 428/835.8; 508/386
(58) Field of Classification Search ........................ None
See application file for complete search history.

(56) References Cited

U.S. PATENT DOCUMENTS

| | | | | |
|---|---|---|---|---|
| 5,037,710 A * | 8/1991 | Frew et al. | ................. | 428/841.3 |
| 2002/0037438 A1 * | 3/2002 | Takami | ................... | 428/694 TF |
| 2002/0119316 A1 * | 8/2002 | Shukla et al. | ................. | 428/408 |
| 2004/0185262 A1 | 9/2004 | Shimokawa | | |

FOREIGN PATENT DOCUMENTS

| | | |
|---|---|---|
| JP | 62-009525 A | 1/1987 |
| JP | 01-106315 A | 4/1989 |
| JP | 04-221426 A | 8/1992 |
| JP | 5-247200 A | 9/1993 |
| JP | 6-150299 A | 5/1994 |
| JP | 7-138359 A | 5/1995 |
| JP | 10-143838 A | 5/1998 |
| JP | 2002-092859 A | 3/2002 |
| JP | 2004-253110 A | 9/2004 |

OTHER PUBLICATIONS

Japanese Office Action issued in Japanese counterpart application No. JP2008-070534, dated Dec. 4, 2012. English translation provided.

* cited by examiner

*Primary Examiner* — Holly Rickman
(74) *Attorney, Agent, or Firm* — Rossi, Kimms & McDowell LLP

(57) ABSTRACT

A magnetic recording medium having high bonding capability between the surface lubricant and the diamond-like carbon (DLC) protective layer in the surface of the magnetic recording medium is disclosed. The lubricant is a fluorine-containing lubricant for magnetic recording media represented by the following formula (1), (2) or (3), wherein the substituents $R^1$, $R^2$, $R^3$, $R^4$, $R^5$ and $R^6$ in the terminal part of the lubricant each independently represent an organic group, and at least one of the substituents $R^1$ and $R^2$, at least one of the substituents $R^3$ and $R^4$, and at least one of the substituents $R^5$ and $R^6$ each have an isocyanate group:

$$R^1-(CF_2CF_2O)_p-(CF_2O)_q-R^2 \quad (1)$$

$$R^3-(CF_2CF_2O)_r-R^4 \quad (2)$$

$$R^5-(CFCF_2O)_s-CFR^6. \quad (3)$$
$$\phantom{R^5-(C}|\phantom{CF_2O)_s-C}|$$
$$\phantom{R^5-(}CF_3\phantom{CF_2O)_s-}CF_3$$

Also disclosed is a magnetic recording medium using the lubricant.

12 Claims, 3 Drawing Sheets

LUBRICANT FOR MAGNETIC RECORDING MEDIA, AND MAGNETIC RECORDING MEDIUM USING THE LUBRICANT

BACKGROUND OF THE INVENTION

A. Field of the Invention

The present invention relates to a lubricant for magnetic recording media, and to a magnetic recording medium for use in magnetic recording devices, in particular a magnetic recording medium for use in external memory devices of computers.

B. Description of the Related Art

A lubricant has been developed which is used in magnetic recording media, especially in magnetic discs for reducing the frictional force to occur between the protective layer thereof and a head and for improving the durability and the reliability thereof. For example, a perfluoropolyether-type lubricant having a polar terminal group such as a hydroxyl group or a cyclic triphosphazene terminal group in the molecule has been applied onto the diamond-like carbon (DLC) protective layer to improve the lubricating characteristics of the surface layer of a magnetic recording medium.

The surface of a diamond-like carbon (DLC) protective layer has a large number of functional groups such as a carboxyl group, a hydroxyl group and an amino group existing therein, and the functional groups positively adsorb and bond to the terminal groups of the above-mentioned lubricant. However, the functional groups have a characteristic of positively adsorbing pollutants such as moisture and acidic gas, as well as the lubricant terminal groups. Accordingly, in cases where the surface of the protective group has free functional groups which are not bonded to the lubricant terminal groups, the adsorption of pollutants may increase.

In order to prevent pollutants such as moisture and acidic gas from being adsorbed by the surface of a disc medium, it is necessary to increase as much as possible the bonding degree (bonding ratio) between the functional groups existing in the carbon surface and the lubricant. See, for example, JP-A-Hei-5-247200 and JP-A-2004-253110 (US family, US 2004/185262A1).

In general, applying a lubricant onto a carbon surface followed by heat treatment may increase the bonding degree between the functional groups on the carbon surface and the lubricant terminal groups. A higher heating temperature in the treatment promotes an increase in the bonding degree between them. However, it is limitative to increase the bonding degree between the functional groups existing in the carbon surface and the lubricant terminal groups. In particular, in the conventional technique of using a perfluoropolyether-type lubricant having a polar terminal group such as a hydroxyl group or a cyclic triphosphazene terminal group in the molecule, a phenomenon of "heating loss" caused by lubricant vaporization from a disc surface is remarkable when the heating temperature is over 100° C.; and this phenomenon becomes more remarkable when the heating temperature is higher. Accordingly, in the high-temperature treatment, the amount of the lubricant existing on a disc surface may be greatly reduced as compared with that before the heat treatment. Therefore, the increase in the bonding degree by heat treatment is limited.

In general, the bonding degree between the functional groups existing in a carbon surface and the terminal groups of a lubricant is represented by the ratio of the thickness of the lubricant layer after washing with a fluorine-containing solvent to the thickness of the lubricant layer before washing with the fluorine-containing solvent, and the percentage is referred to as "bonding ratio":

$$\text{Bonding Ratio [\%]} = \frac{\text{lubricant layer thickness after washing}}{\text{lubricant layer thickness before washing}} \times 100$$

In this definition, the lubricant layer thickness before washing is referred to as "total lubricant layer thickness," the lubricant layer thickness after washing is as "bonding lubricant layer thickness," and the difference between the total lubricant layer thickness and the bonding lubricant layer thickness is the "free lubricant layer thickness." The "bonding lubricant layer thickness" represents the thickness (amount) of the lubricant actually bonding to a carbon surface, and to inhibit the pollutant adsorption, this amount must be increased.

The "bonding ratio" standard is described. In cases where Vertrel XF (by Mitsui DuPont Fluorochemical) is used as a fluorine-containing solvent and when a perfluoropolyether-type lubricant having a polar terminal group such as a hydroxyl group or a cyclic triphosphazene terminal group in the molecule (e.g., Fomblin Z-Tetraol, by Solvay Solexis) of the prior art is used, the uppermost limit of the bonding ratio may be about 70% for the reasons mentioned above (JP-A-Hei-10-143838). In this case, when the total lubricant layer thickness is 1.0, 1.2 or 1.4 nm, which is, at present, an ordinary lubricant layer thickness in ordinary hard discs, then the bonding lubricant layer thickness is 0.7, 0.84 or 0.98 nm, respectively.

On the other hand, with the recent tendency toward high-density magnetic discs, the requirements of lubricant characteristics have become more severe. To satisfy the requirements, in future, the uppermost limit of the bonding lubricant layer thickness must be increased even more.

In addition, regarding the recent application mode of hard disc drives, not only the conventional mainstream uses thereof for indoor personal computers, but also their outdoor applications for mobile devices, car navigation systems and others, are increasing. In particular, often problematic is a phenomenon of difficult floating of magnetic head sliders in high-temperature high-humidity environments, and this may be the result of aggregation of moisture existing in high-humidity air. Accordingly, it is a significant problem how to reduce the amount of moisture that adheres to and aggregates on the surface of a magnetic disc, in other words, how to hydrophobicate the disc surface.

Hydrophobication requires an increase in the bonding lubricant layer thickness and, in cases where the uppermost limit of the bonding ratio is defined, a simple increase in the total lubricant layer thickness may be enough for the increase in the bonding lubricant layer thickness. However, a simple increase in the layer thickness may often bring about a phenomenon of lubricant pickup by the floating slider, therefore causing a problem of slider floating instability.

Accordingly, a method of increasing the bonding ratio between the lubricant and the carbon surface as compared with that in a conventional method is required instead of changing the total lubricant layer thickness therein.

The present invention is directed to overcoming or at least reducing the effects of one or more of the problems set forth above.

SUMMARY OF THE INVENTION

Therefore, in view of the above-mentioned problems, the invention provides a magnetic recording medium having high adsorbability between a lubricant and the surface of the diamond-like carbon (DLC) protective layer thereof, as compared with that in conventional techniques.

In one aspect thereof, the invention relates to a fluorine-containing lubricant. The lubricant is a fluorine-containing lubricant for magnetic recording media, represented by the following formula (1), (2) or (3):

Formula 1

wherein p and q each indicate a positive integer

Formula 2

wherein r indicates a positive integer

Formula 3

wherein s indicates a positive integer.

The substituents $R^1$, $R^2$, $R^3$, $R^4$, $R^5$ and $R^6$ in the terminal part of the lubricant each independently represent an organic group, and at least one of the substituents $R^1$ and $R^2$, at least one of the substituents $R^3$ and $R^4$, and at least one of the substituents $R^5$ and $R^6$ each have an isocyanate group.

Another aspect of the invention is a magnetic recording medium using the above-mentioned lubricant. More particularly, the magnetic recording medium of the invention has at least a magnetic layer, a protective layer and a lubricant layer on a nonmagnetic substrate, wherein the lubricant layer contains a lubricant represented by the above formula (1), (2) or (3).

In the aspects of the invention as above, it is preferable that the substituents $R^1$, $R^2$, $R^3$, $R^4$, $R^5$ and $R^6$ in the terminal part each independently have a skeleton selected from a group consisting of a saturated or unsaturated hydrocarbon, an aromatic hydrocarbon, an aromatic amine, a hetero ring, a heterocyclic amine and their combination.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

Applying the lubricant of the invention onto a diamond-like carbon (DLC) protective layer makes it possible to provide a magnetic recording medium having high bonding capability between the lubricant and the surface of the diamond-like carbon (DLC) protective layer thereof, as compared with that in conventional techniques.

In one aspect thereof, the invention relates to a lubricant for magnetic recording medium. The lubricant is a fluorine-containing lubricant for magnetic recording media, represented by the following formula (1), (2) or (3):

wherein p and q each indicate a positive integer; preferably p is from 3 to 60, and q is from 3 to 60

wherein r indicates a positive integer; preferably r is from 3 to 60

wherein s indicates a positive integer; preferably s is from 3 to 100.

The substituents $R^1$, $R^2$, $R^3$, $R^4$, $R^5$ and $R^6$ in the terminal part each independently represent an organic group. Concretely, it is desirable that these groups are independently selected from a group consisting of a saturated or unsaturated hydrocarbon having a carbon number of 1 to 50, preferably 1 to 20, an aromatic hydrocarbon, an aromatic amine, a hetero ring and a heterocyclic amine. The substituents may have one or more those skeletons singly or as combined. In the invention, at least one of the substituents $R^1$ and $R^2$, at least one of the substituents $R^3$ and $R^4$, and at least one of the substituents $R^5$ and $R^6$ each have an isocyanate group.

The lubricant of the invention represented by the above formulae (1) to (3) may be applied to the surface of a magnetic recording medium (magnetic disc) according to various methods, such as dipping or spin coating. The lubricant of the invention may enhance the bonding capability between the terminal substituents of the lubricant molecule and a large number of functional groups such as a carboxyl group, a hydroxyl group and an amine group existing in the surface of a protective group. A perfluoropolyether compound, Demnum (by Daikin) is preferred for the backbone structure of the lubricant of the invention, and the lubricant is characterized by having an isocyanate group as the substituent in its terminal part.

Applying the lubricant of the invention onto the surface of a magnetic recording medium realizes a magnetic recording medium having high bonding capability between the lubricant and the protective layer thereof, as compared with conventional lubricants.

Figure 1:
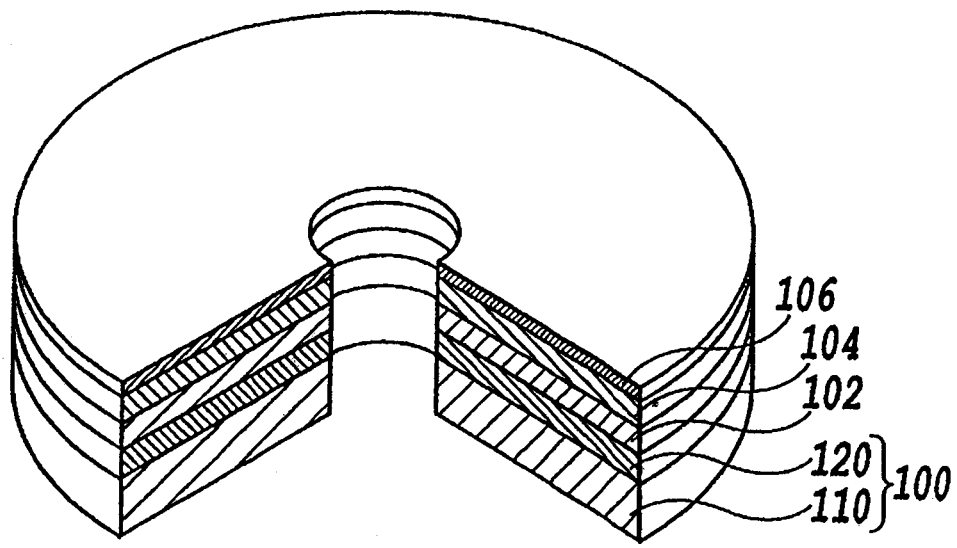
FIG. 1 is a schematic view showing a typical layer constitution of the magnetic recording medium of the invention.

Next a magnetic recording medium of the invention is described. The magnetic recording medium of the invention has at least a magnetic layer, a protective layer and a lubricant layer on a nonmagnetic substrate. As one example, this has a structure shown in FIG. 1, with magnetic layer 102, protective layer 104 and lubricant layer 106 on nonmagnetic substrate 100.

The nonmagnetic substrate is not specifically defined, and may be any one heretofore used in magnetic recording media. For example, it may comprise nonmagnetic metal layer (plating layer) 120 of Ni—P or the like formed by electroless plating on substrate 110 of an aluminium alloy or the like heretofore generally used in the art, as in FIG. 1; or may be formed of a material such as glass, ceramics or plastics.

If desired, the magnetic recording medium of the invention may have a nonmagnetic undercoat layer, a soft magnetic layer, a seed layer, an interlayer and the like formed between the nonmagnetic substrate and the magnetic layer. The optional nonmagnetic undercoat layer may be formed of Ta, Ti or a Cr-containing nonmagnetic material such as a CrTi alloy.

The optional soft magnetic layer may be formed of a crystalline material such as FeTaC or sendust (FeSiAl) alloy; a microcrystalline material such as FeTaC, CoFeNi or CoNiP; of an amorphous material containing a Co alloy such as CoZrNd, CoZrNb or CoTaZr. The soft magnetic layer is for concentrating the vertical magnetic field to the magnetic layer, and its optimum thickness varies depending on the structure and the characteristics of the magnetic head to be used in recording. In general, the thickness is preferably from 10 nm to 500 nm from the viewpoint of the good balance thereof with the producibility.

The optional seed layer may be formed of a metal or alloy having a face-centered cubic lattice structure, or of Ta or a Ta alloy. The metal or alloy having a face-centered cubic lattice structure includes Cu, Pd, Pt, Ni and an alloy comprising at least one of these; a permalloy material such as NiFe, NiFeNb, NiFeCr, NiFeSi or NiFeB; a material prepared by further adding Ca to a permalloy material, such as CoNiFe, CoNiFeNb, CoNiFeCr, CoNiFeSi or CoNiFeB; Co; and a Co-base alloy such as CoB, CoSi, CoNi or CoFe. Preferably, the seed layer is thick enough to control the crystal structure of the magnetic layer; and in general, its thickness is preferably from 3 nm to 50 nm.

The optional interlayer may be formed of Ru or a Ru-based alloy, or Co or a Co-based alloy. The metal or alloy may be laminated. The interlayer generally has a thickness of from 0.1 nm to 30 nm. With a thickness that falls within this range, the interlayer will not have any negative influence on the magnetic characteristics and the electromagnetic conversion characteristics of the magnetic layer, and the magnetic layer will have the properties necessary for high-density recording.

The nonmagnetic undercoat layer, the soft magnetic layer, the seed layer and the interlayer mentioned above may be formed by any method known in the art, for example, by a sputtering method (including a DC magnetron sputtering method, an RF magnetron sputtering method), a vacuum evaporation method, or the like.

Preferably, the magnetic layer is formed of a ferromagnetic material of an alloy containing at least Co and Pt. For vertical magnetic recording therein, the material of the magnetic layer must be such that the easy magnetization axis (the c axis of the hexagonal closest packing (hcp) structure) thereof is oriented in the direction vertical to the surface of the recording medium, that is, the main surface of the magnetic recording medium substrate. The magnetic layer may be formed of, for example, an alloy material such as CoPt, CoCrPt, CoCrPtB or CoCrPtTa. The thickness of the magnetic layer is not specifically defined. However, from the viewpoint of good producibility and high recording density, the magnetic layer preferably has a thickness of at most 30 nm, more preferably at most 15 nm. The magnetic layer may be formed by any method known in the art, for example, by a sputtering method (including a DC magnetron sputtering method, an RF magnetron sputtering method), a vacuum evaporation method or the like.

Alternatively, the magnetic layer may be formed of a material having a granular structure and comprising magnetic crystal particles dispersed in a matrix of nonmagnetic oxide or nonmagnetic nitride. The material having a granular structure includes $CoPt-SiO_2$, $CoCrPt-TiO_2$, $CoCrPtO$, $CoCrPt-SiO_2$, $CoCrPt-Al_2O_3$, $CoPt-AlN$, $CoCrPt-Si_3N_4$ and the like, to which, however, the invention should not be limited. Use of a material having a granular structure promotes magnetic separation of neighboring magnetic crystal particles in the magnetic layer, thereby improving the magnetic recording characteristics of the layer for noise reduction, an increase in SNR and an increase in recording resolution.

The protective layer may be formed of carbon, e.g., diamond carbon or amorphous carbon, or of various thin-layer materials known as materials for protective layers of magnetic recording media. The protective layer is for protecting various constitutive layers such as magnetic layer and others. In general, the protective layer may be formed by a sputtering method (including DC magnetron sputtering method, RF magnetron sputtering method), a vacuum evaporation method, a CVD method or the like.

The lubricant layer is a layer for providing lubricity between a recording/reading head and the magnetic recording medium when in contact with each other, and this may be formed of the lubricant of the invention mentioned in the above. The lubricant layer may be formed by any method known in the art, for example, by dipping, spin coating, or the like.

EXAMPLES

The invention is described in more detail with reference to the following Examples, which, however, are not intended to restrict the scope of the invention.

1. Method for Producing Lubricant of the Invention:

Production of the fluorine-containing lubricant of the invention (Compound (A)) terminated with an isocyanate group is described.

Production Example

An isocyanate group-terminated fluorine-containing lubricant (Compound (A)) was produced in the manner mentioned below.

$RfCH_2OH + OCN(CH_2)_6NCO \rightarrow RfCH_2OCONH(CH_2)_6NCO$ 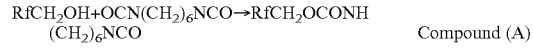 Compound (A)

A hydroxyl group (—OH)-terminated perfluoropolyether, Daikin Industry's Demnum SA (50.0 g) ($RF=CF_3CF_2CF_2O-(CF_2CF_2CF_2O)_n-CF_2CF_2-$) and hexamethylene diisocyanate (22.7 g) were dissolved in m-xylene-hexafluoride (200 g). The solution was heated up to 90° C., and then 1,4-diazabicyclo[2,2,2]octane (76 mg) was added thereto. The reaction mixture was stirred for 3 hours while being kept at 130° C. NMR confirmed the end point of the reaction. N-xylene-hexafluoride was evaporated away under reduced pressure from the resulting reaction mixture, and diethyl ether was added to the resulting concentrate and stirred. After statically left as such for layer separation, the lower layer was collected and processed for reduced pressure distillation to obtain the intended, isocyanate group-terminated perfluoropolyether (Compound (A)) (36.6 g).

I. Production of Magnetic Recording Medium (Sample):

In the Examples and Comparative Example, a lubricant layer was formed by the use of the Compound (A) (mean molecular weight, 3800) produced in the above-mentioned production method, on a diamond-like carbon (DLC) protective layer formed according to a plasma CVD method of a magnetic recording medium.

A nonmagnetic undercoat layer of CrTi having a thickness of 2 nm, a soft magnetic layer of CoZrNb having a thickness of 50 nm, a seed layer of CoNiFeSi having a thickness of 5 nm, an interlayer of Ru having a thickness of 190 nm, and a magnetic layer of $CoCrPt-SiO_2$ and CoCrPrB having a thickness of 16 nm were formed in that order by a sputtering method on the main surface of a nonmagnetic substrate (magnetic disc substrate of an Al alloy material having a diameter of 95 mm).

Next, a DLC protective layer having a thickness of 3.0 nm was formed according to a plasma CVD method. A lubricant solution of the Compound (A) produced in the above-mentioned production method was applied to the protective layercovered magnetic disc substrate by dipping. Then, the disc substrate was dipped in a lubricant solution in a solvent of Vertrel XF for 180 seconds, and the magnetic disc was pulled up at a rate of 1.5 mm/sec, and thereafter this was dried at room temperature 22° C.

For comparison, a conventional lubricant, Z-Tetraol (by Solvay Solexis) was applied to the substrate according to the same dipping method.

The concentration of the lubricant used in producing the samples according to the above-mentioned method is shown in Table 1.

II. Evaluation of Magnetic Recording Medium:

II-1. Bonding Ratio

The samples produced in the above I were analyzed for the lubricant layer thickness (total lubricant layer thickness and bonding lubricant layer thickness) before and after washing, and the bonding ratio was computed. The results are shown in Table 1. The thickness of the lubricant layer was measured with a Fourier transform IR spectrometer (FT-IR).

Vertrel XF (by Mitsui DuPont Fluorochemical) is generally used as the fluorine-containing solvent for washing away lubricant, generally used, and the solvent was used in this evaluation. For washing the samples, the fluorine-containing solvent was applied to the samples at 22° C. for 5 minutes by a dipping method.

From the results in Table 1 and Table 2, it is known that the heat treatment increased the bonding lubricant layer thickness and the bonding ratio of all the samples. However, under the process condition employed herein, the conventional lubricant-coated sample (Comparative Example 2) had a bonding lubricant layer thickness of 0.643 nm and its bonding ratio increased up to 52%. The samples coated with the lubricant of the invention had better results than the conventional lubricant-coated sample. For example, the sample of Example 4 having nearly the same total lubricant layer thickness before and after heating had an increased bonding lubricant layer thickness of 1.167 nm and an increased bonding ratio of 86% after heating, or that is, the lubricant of the invention produced better results than the conventional lubricant.

Comparative Example 1 was compared with Comparative Example 2, and Example 2 was compared with Example 4 both in point of the total lubricant layer thickness of the samples. In the Comparative Examples, the total lubricant layer thickness reduced by 0.146 nm before and after heating; but in the Examples where the lubricant of the invention was used, the reduction was only 0.03 m before and after heating. This confirms the lubricant of the invention gives little heating loss.

TABLE 1

| | Lubricant | Lubricant Solution Concentration [wt. %] | Total Lubricant Layer Thickness [nm] | Bonding Lubricant Layer Thickness [nm] | Bonding Ratio [%] |
|---|---|---|---|---|---|
| Comparative Example 1 | Z-Tetraol | 0.06 | 1.39 | 0.332 | 24 |
| Example 1 | Compound (A) | 0.009 | 1.02 | 0.685 | 67 |
| Example 2 | Compound (A) | 0.116 | 1.380 | 0.878 | 64 |

From Table 1, it is known that the lubricant of the invention, Compound (A) realized a thicker bonding lubricant layer thickness that of the conventional lubricant, at the end of the coating step. For example, Comparative Example 1 is compared with Example 2. It is known that, the total lubricant layer thickness is nearly the same in the two, but in Example 2 where the lubricant of the invention was used, the bonding lubricant layer thickness produced a difference of 2.6 times higher than that in Comparative Example 1 where the conventional lubricant was used.

II-2. Heating Loss Evaluation

Before the test of measuring the total lubricant layer thickness thereof, the samples produced in the above I were heated in a furnace at 110° C. for 60 minutes. After the heat treatment, the total lubricant layer thickness, the bonding lubricant layer thickness and the bonding ratio of the samples were determined, and the data are shown in Table 2. The method of layer thickness measurement and the method of washing are the same as in the above II-1.

II-3. Spin-Off Evaluation

The samples produced in the process of the above-mentioned II-2 and shown in Table 2 (lubricant-coated and heated samples) were tested in a spin-off test. The spin-off test is as follows: A disc sample is rotated at a high rotation speed for a long period of time, and after the rotation test, the sample is analyzed for the movement of the lubricant layer thereof. In this test, the lubricant layer moves from the inner peripheral side to the outer peripheral side owing to the centrifugal force during rotation. In case where the bonding between the lubricant and the carbon protective film is stronger, the movement may be inhibited more.

In this test, the disc sample was rotated at 7200 rpm for 14 days in an environment at a temperature of 40° C. and at a humidity of 80%, and then the movement of the lubricant layer was measured with OSA (Optical Surface Analyzer, scanning ellipsometer). The found data are given in FIG. 2 to FIG. 4, which show the lubricant layer distribution after the test.

TABLE 2

| | Lubricant | Total Lubricant Layer Thickness [nm] | Bonding Lubricant Layer Thickness [nm] | Bonding Ratio [%] |
|---|---|---|---|---|
| Comparative Example 2 | Z-Tetraol | 1.244 | 0.643 | 52 |
| Example 3 | Compound (A) | 0.985 | 0.865 | 88 |
| Example 4 | Compound (A) | 1.350 | 1.167 | 86 |

Figure 2:
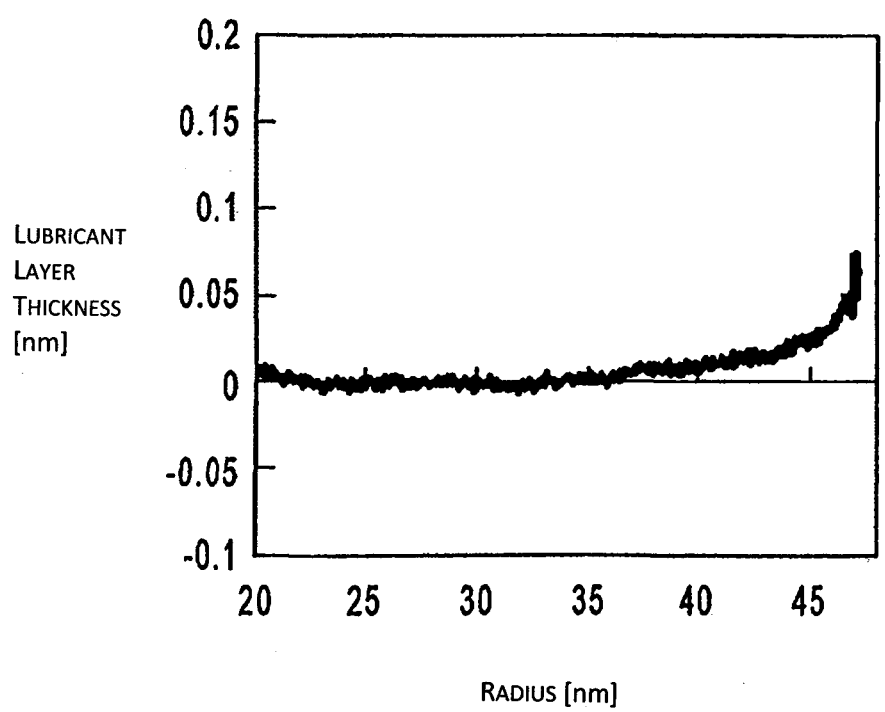
FIG. 2 is a graph showing the lubricant layer distribution after a spin-off test of a magnetic recording medium using a conventional lubricant (Comparative Example 2).
Figure 3:
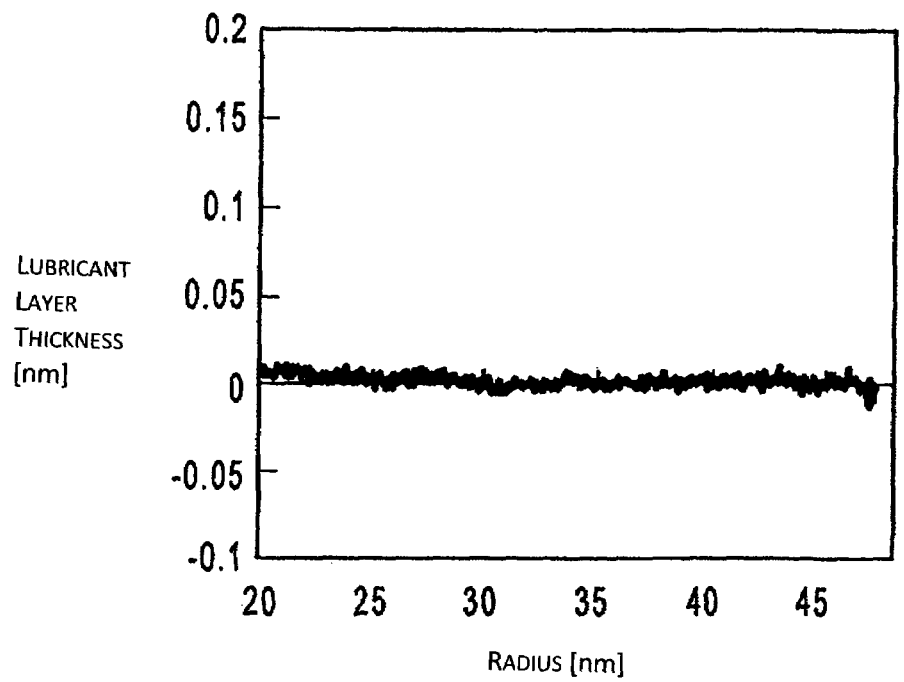
FIG. 3 is a graph showing the lubricant layer distribution after a spin-off test of a magnetic recording medium using a lubricant of the invention (Example 3).
Figure 4:
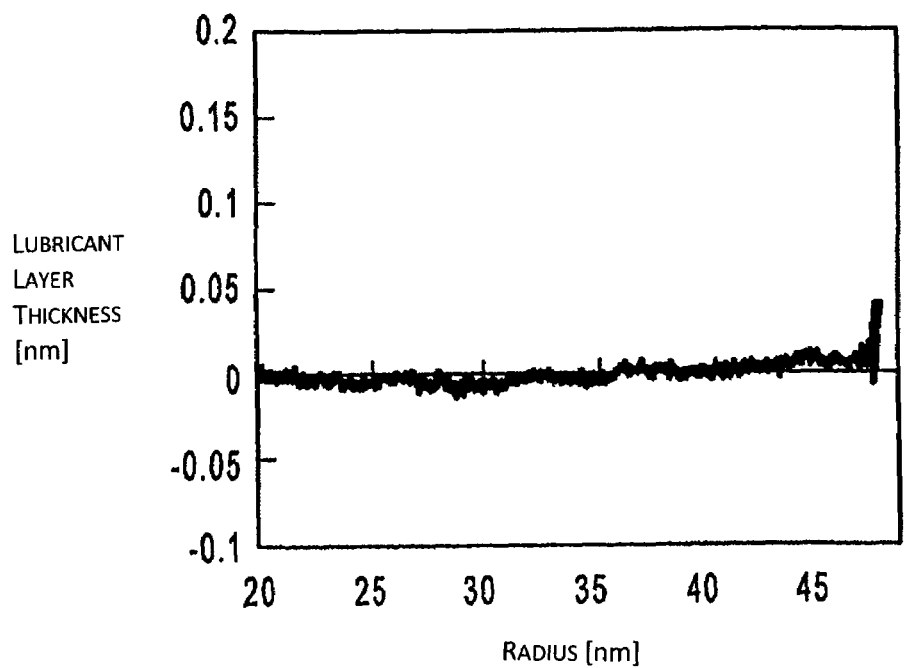
FIG. 4 is a graph showing the lubricant layer distribution after a spin-off test of a magnetic recording medium using a lubricant of the invention (Example 4).

FIG. 2 (Comparative Example 2), FIG. 3 (Example 3) and FIG. 4 (Example 4) are compared with each other. Obviously, in the sample coated with the conventional lubricant, the thickness of the coating layer increased on the outer peripheral side, and this indicates the movement of the lubricant. As opposed to this, in the samples coated with the lubricant of the invention, little movement of the lubricant layer by the centrifugal force was found.

From the above results, it may be said that the lubricant of the invention bonds more strongly to the carbon protective layer than the conventional lubricant.

II-4. Contact Angle Evaluation

For evaluating the hydrophilicity of the disc surface, the samples were tested for their contact angle with water. The samples are the discs of the above II-2 (lubricant-coated and heated samples). The data are given in FIG. 5, which indicates the relationship between the contact angle and the bonding lubricant layer thickness. In the drawing, 1 is the result of the sample using the conventional lubricant, Z-Tetraol (Comparative Example 2), 2 is the result of the sample using the lubricant of the invention (Example 3), and 3 is the result of the sample using the lubricant of the invention (Example 4).

Figure 5:
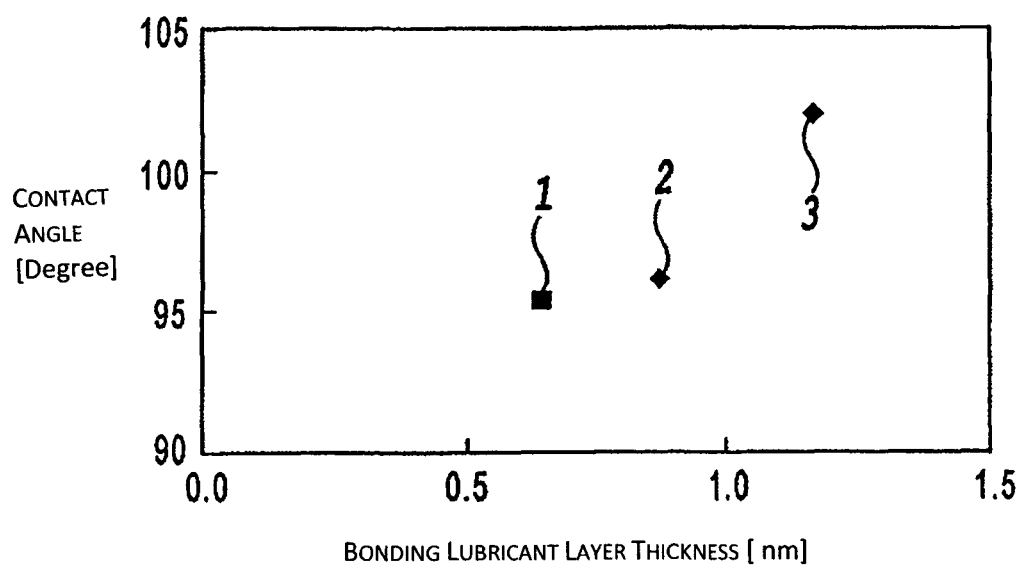
FIG. 5 is a graph showing the relationship between the contact angle with water and the bonding lubricant layer thickness of a magnetic recording medium using a conventional lubricant (Comparative Example 2), and a magnetic recording medium using a lubricant of the invention (Example 3 and Example 4).

From FIG. 5, it is known that the contact angle depends on the bonding lubricant layer thickness or, that is, a sample having a larger bonding lubricant layer thickness has a larger contact angle, and therefore has a hydrophobic surface.

In a case where the lubricant of the invention is used under the same process condition, the lubricant layer formed may have a larger bonding lubricant layer thickness than that in a case where a conventional lubricant is used; and therefore, different from the related conventional technique, the invention can realize a hydrophobic surface.

Compounds similar to the Compound (A), in which Rf is the following (A)' or (A)", also have nearly the same characteristics as those of the Compound (A).

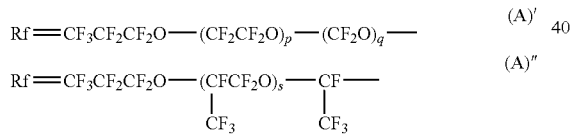

Thus, a lubricant for magnetic recording media and a magnetic recording medium for use in magnetic recording devices has been described according to the present invention. Many modifications and variations may be made to the techniques and structures described and illustrated herein without departing from the spirit and scope of the invention. Accordingly, it should be understood that the media and methods described herein are illustrative only and are not limiting upon the scope of the invention.

This application is based on and claims priority to Japanese Patent Application 2008-070534, filed on Mar. 19, 2008. The disclosure of the priority application in its entirety, including the drawings, claims, and the specification thereof, is incorporated herein by reference.

What is claimed is:

1. A fluorine-containing lubricant for magnetic recording media represented by the following formula (2) or (3),

wherein r indicates a positive integer,

wherein s indicates a positive integer, wherein the substituents $R^3$, $R^4$, $R^5$ and $R^6$ in the terminal part of the lubricant each independently represent an organic group, and at least one of the substituents $R^3$ and $R^4$, and at least one of the substituents $R^5$ and $R^6$ each is $CH_2OCONH(CH_2)_6NCO$.

2. The lubricant as claimed in claim 1, wherein the $R^3$ or $R^4$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination and wherein the $R^5$ or $R^6$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

3. A magnetic recording medium having at least a magnetic layer, a protective layer and a lubricant layer on a nonmagnetic substrate, wherein the lubricant layer contains a lubricant represented by the following formula (2) or (3), and wherein the substituents $R^3$, $R^4$, $R^5$ and $R^6$ in the terminal part of the lubricant each independently represent an organic group, and at least one of the substituents $R^3$ and $R^4$, and at least one of the substituents $R^5$ and $R^6$ each is $CH_2OCONH(CH_2)_6NCO$:

wherein r indicates a positive integer,

wherein s indicates a positive integer.

4. The magnetic recording medium as claimed in claim 3, wherein the $R^3$ or $R^4$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination and wherein the $R^5$ or $R^6$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

5. The lubricant as claimed in claim 1, represented by formula (2).

6. The lubricant as claimed in claim 5, wherein the $R^3$ or $R^4$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

7. The lubricant as claimed in claim 1, represented by formula (3).

8. The lubricant as claimed in claim 7, wherein the $R^5$ or $R^6$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

9. The magnetic recording medium as claimed in claim 3, wherein the lubricant is represented by formula (2).

10. The magnetic recording medium as claimed in claim 9, wherein the $R^3$ or $R^4$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

11. The magnetic recording medium as claimed in claim 3, wherein the lubricant is represented by formula (3).

12. The magnetic recording medium as claimed in claim 11, wherein the $R^5$ or $R^6$ substituent that is not $CH_2OCONH(CH_2)_6NCO$ has a skeleton selected from a group consisting of a saturated or unsaturated hydrocarbon, an aromatic hydrocarbon, an aromatic amine, a hetero ring, a heterocyclic amine and their combination.

* * * * *